United States Patent [19]

Schebler

[11] Patent Number: 4,499,914

[45] Date of Patent: Feb. 19, 1985

[54] SELECTOR VALVE FOR AN AIRCRAFT ON BOARD OXYGEN GENERATION SYSTEM WITH HIGH PRESSURE OXYGEN BACKUP

[75] Inventor: Bernard J. Schebler, Davenport, Iowa

[73] Assignee: Litton Systems, Inc., Davenport, Iowa

[21] Appl. No.: 484,964

[22] Filed: Apr. 14, 1983

[51] Int. Cl.[3] .............................................. A61M 15/00

[52] U.S. Cl. .............................. 137/81.1; 137/505.28; 137/112; 128/204.21; 128/204.29

[58] Field of Search ...................... 137/111, 112, 81.1, 137/505.28; 128/204.21, 204.29

[56] References Cited

U.S. PATENT DOCUMENTS

| | | | |
|---|---|---|---|
| 441,648 | 12/1890 | Curtis | 137/505.28 |
| 3,103,927 | 9/1963 | Henneman | 137/81.1 |
| 3,179,119 | 4/1965 | Fitt et al. | 137/81.1 |
| 3,672,384 | 6/1972 | Hellquist | 137/81.1 |
| 3,875,957 | 4/1975 | Veit et al. | 137/81.1 |
| 4,148,311 | 4/1979 | London et al. | 128/204.29 |
| 4,282,870 | 8/1981 | Porlier | 128/204.29 |
| 4,335,735 | 6/1982 | Cramer et al. | 137/81.1 |
| 4,336,590 | 6/1982 | Jacq et al. | 128/204.21 |

*Primary Examiner*—A. Michael Chambers
*Attorney, Agent, or Firm*—Brian L. Ribando

[57] ABSTRACT

A selector valve for an aircraft breathing system wherein oxygen enriched gas is provided by two sources, the primary source being fractionalized air and the secondary, backup, source being bottled oxygen is comprised of a control valve with three operating modes and a shuttle valve. In the first operating mode gas is provided from the primary source, in the second operating mode gas is provided from the primary source within certain operating parameters and outside these parameters gas from the secondary source is provided. In the third operating mode, gas from the secondary source is provided. The shuttle valve responds to the secondary source gas pressure and directs gas from either source to the pilot based on preset conditions.

5 Claims, 2 Drawing Figures

SELECTOR VALVE FOR AN AIRCRAFT ON BOARD OXYGEN GENERATION SYSTEM WITH HIGH PRESSURE OXYGEN BACKUP

BACKGROUND OF THE INVENTION

High altitude aircraft require oxygen enriched air either as emergency backup in the event of loss of cabin pressure as in commercial transports or as an on-line system which controls oxygen enrichment as a function of altitude and other parameters as in military aircraft. Oxygen enrichment can be achieved using oxygen sources such as stored liquid oxygen, high pressure oxygen gas, oxygen generators, sometimes referred to as candles, or fractionalized air. Except in the case of fractionalizing air, the oxygen source represents a discreet quantity limited by storage capacity and/or weight which can be critical in airborne applications. Air fractionalizing is a continuous process, and, thus, represents advantages where capacity, supply logistics, or weight are problems.

Air fractionalizing is normally accomplished by alternating the flow of high pressure air through each of two beds containing a molecular sieve material such as zeolite. This process is identified as the pressure swing adsorption technique and it employs a myriad components, mechanical, electrical and pneumatic. Though highly reliable, the number of components making up a pressure swing system suggests the probability of an intermittent failure. In high altitude military aircraft, where a single such failure could be catastrophic, it is very desirable to maintain a backup system usually comprised of high pressure oxygen bottles. This high pressure gas can also be used at very high altitudes to achieve oxygen concentrations above those attainable by pressure swing adsorption systems due to the trace gases such as argon which are not adsorbed and exit the adsorption system as part of the product gas.

In an aircraft using an air fractionalizing oxygen enriching system with high pressure bottled oxygen backup, various modes of operation of the two systems in combination are possible. These modes include operation from the bottled gas, from the fractionalized air, or an automatic mode in which either of the two sources is selected based on altitude, oxygen concentration in the breathing system and/or breathing system pressure.

SUMMARY AND OBJECTS OF THE INVENTION

According to the invention, a selector valve for a high altitude aircraft on-board oxygen generating system (OBOGS) with high pressure bottled oxygen backup is used to combine the various mechanical, electrical, and pneumatic elements of this breathing system to best sit the flight regime of the aircraft at any particular time.

It is therefore an object of this invention to provide an aircraft breathing system utilizing an air fractionalizing primary source of oxygen enriched product gas and bottled high pressure oxygen as a backup source for emergency oxygen, as well as higher oxygen concentration product gas.

It is also an object of the invention to provide a selector valve for combining the various mechanical, electrical, and pneumatic elements of the breathing system to adapt its mode of operation to the aircraft flight parameters and the pilot needs.

It is still a further object of the invention to provide a selector valve which will automatically select the backup oxygen source if the oxygen partial pressure ($PPO_2$) or the OBOGS system pressure falls below a predetermined level in the breathing system.

It is yet another object of the invention to provide a selector valve which will automatically select OBOGS gas upon depletion of the backup oxygen below a predetermined pressure.

DETAILED DESCRIPTION OF THE PREFERRED EMBODIMENT

Figure 1:
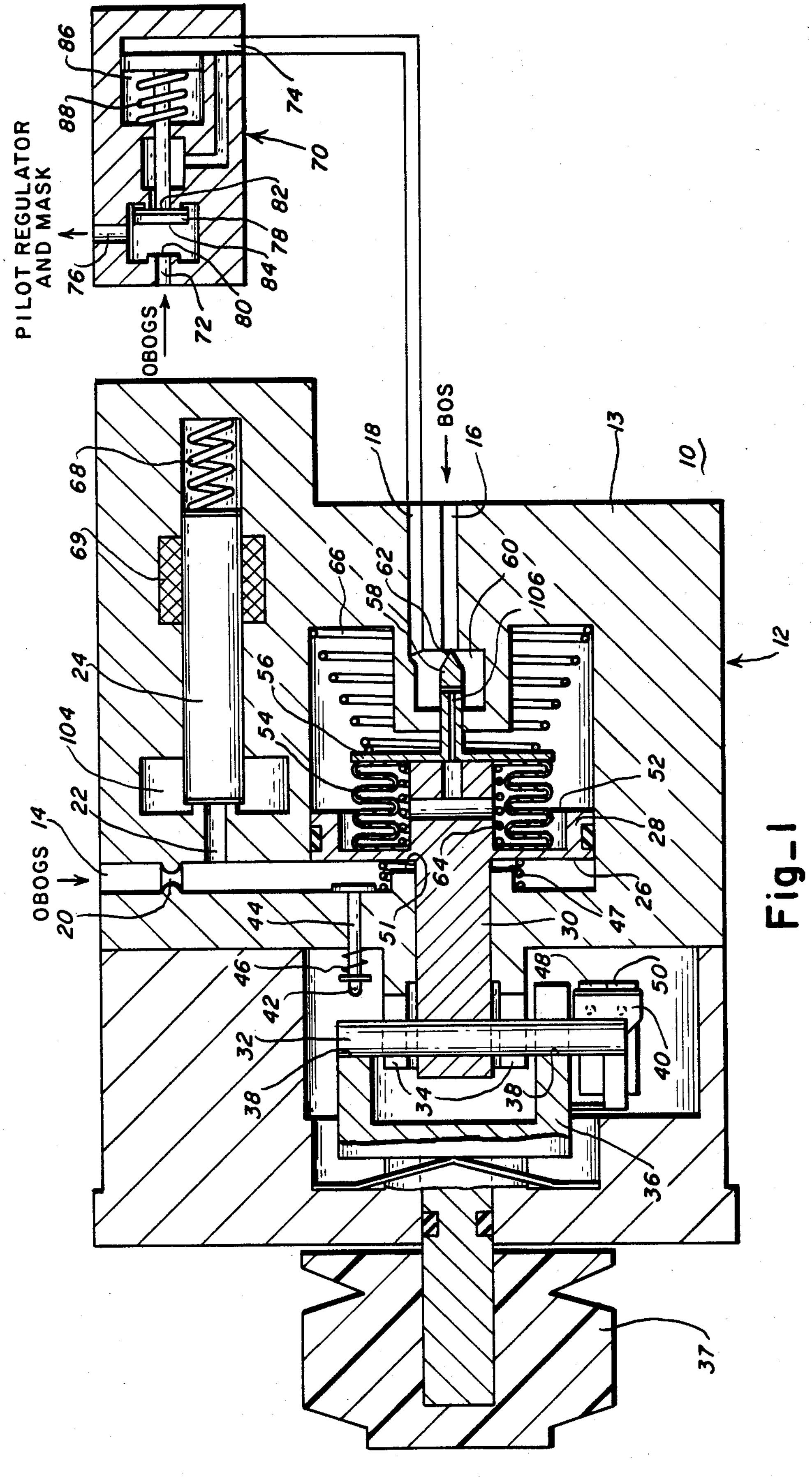
FIG. 1 is a schematic representation of a selector valve for an aircraft oxygen enriched breathing system employing both air fractionalization and bottled gas as oxygen sources.

A selector valve 10, as illustrated in FIG. 1, for use in an aircraft breathing system wherein oxygen enrichment is provided by two sources, fractionalized air and backup bottled gas includes a control valve 12 and a shuttle valve 70. The control valve 12 has three pneumatic ports, an inlet port 14 through which the product gas of the air fractionalizing on-board oxygen generating system (OBOGS) flows, a bottled gas inlet port 16, and a regulated pressure outlet 18 for the backup bottled gas. The OBOGS gas entering the port 14 passes through a flow restrictor 20 to the inlet port 22 of a normally closed solenoid valve 24 and to the first face 26 of a piston 28. The piston 28 has an integral stem 30 with a roll pin 32 rigidly secured at one end perpendicular to the axis of the stem. The roll pin 32 is guided in slots 34 in the housing 13 preventing the stem 30 from rotating while allowing it to move axially. Axial motion of the stem 30 occurs as the screw cam 36 rotates with its cam surfaces 38 engaging the roll pin 32. The roll pin 32 is held in engagement with the cam surfaces 38 by the bias of a compression spring 66.

The axial travel of the roll pin 32 simultaneously actuates two microswitches 48 and 50 as the roll pin engages a trip lever 40 when the roll pin is driven into the valve (which motion in the exemplary illustration is to the right). As the screw cam 36 rotates so as to allow the roll pin 32 to move in the opposite direction (to the left), a crest of one of the screw cam lobes engages the stem 42 of a dump valve 44 opening it against the bias of a compression spring 46.

A biasing spring 47 acts on the first face 26 to effectively lower the OBOGS gas pressure downstream of the flow restrictor 20 at which the piston 28 is displaced.

On the second face 52 of the piston 28, there is mounted a sealed bellows 54. The bellows end opposite the piston 28 is sealed by an end plate 56 integral with a poppet 58. The poppet 58 is sealed as it passes through the housing 13 into a closed chamber 60 allowing it to modulate or restrict the flow of backup oxygen from the inlet port 16 to the exit port 18 as the poppet 58 constricts or stops the flow through an area 62.

The bellows 54 is biased in a first direction by a compression spring 64 and in a second direction by a compression spring 66, which also biases the piston 28, its stem 30 and the roll pin 32.

The normally closed solenoid 24 is biased in the closed position by a compression spring 68 and is opened against the compression load of that spring when the coils 69 are electrically excited.

The shuttle valve 70 also has three ports, an inlet port 72 through which the OBOGS gas enters, a backup oxygen inlet port 74 which is connected to the pressure regulated outlet port 18 of the control valve 12, and a discharge port 76 which is connected to a breathing mask regulator (not shown) which breathing mask furnishes the oxygen enriched gas to the pilot. Gas flow through the shuttle valve 70 is controlled by a piston 78 alternatively seating and closing or unseating and opening inlets 80 and 82 to a chamber 84 which communicates with the discharge port 76. The piston 78 is connected to a second piston 86 which is biased by a spring 88. The piston 86 is responsive to the backup oxygen pressure at the port 74 acting against the spring 88 bias.

Figure 2:
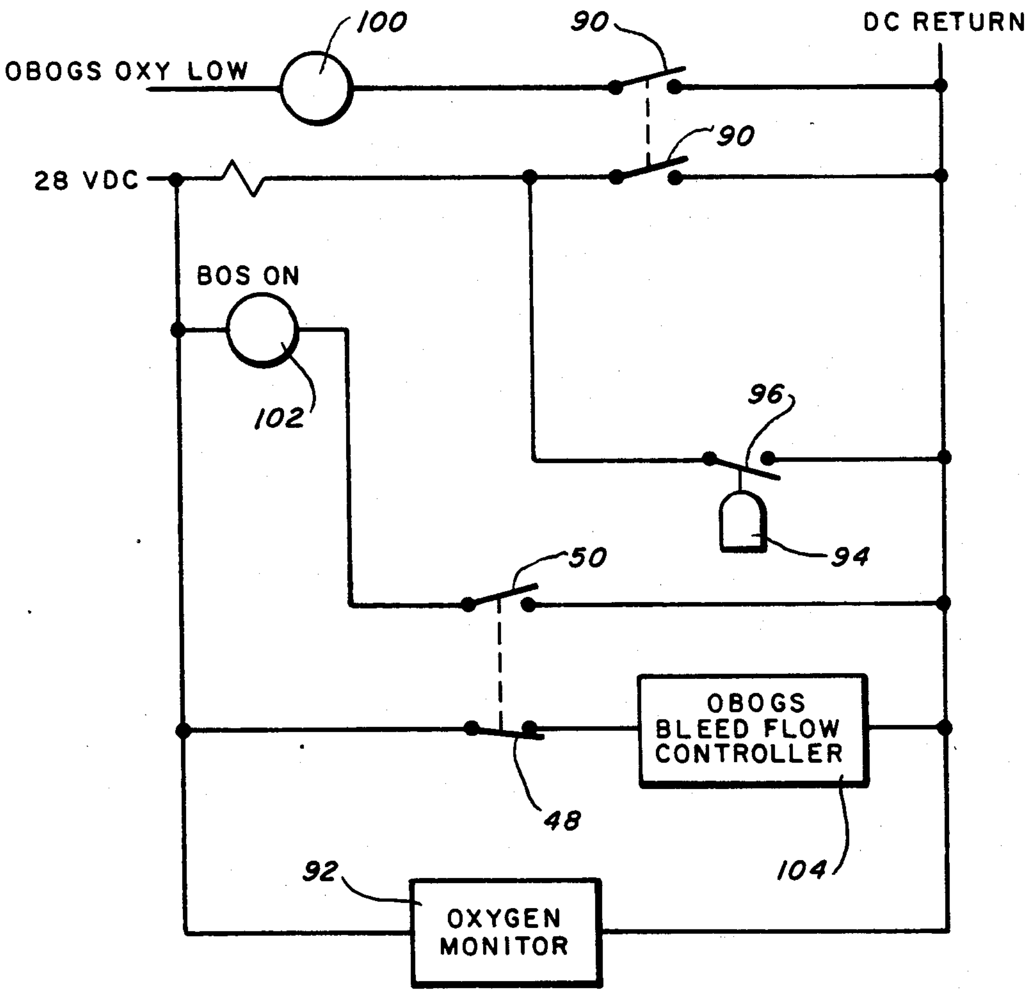
FIG. 2 is an electrical schematic for energizing the control valve coil and powering system performance indicator lamps.

The selector valve 10 is an electromechanical/-pneumatic device. The electrical control circuit focuses primarily on energizing the coils 69 of the solenoid valve 24. FIG. 2 schematically represents the electrical circuitry. The microswitches 48 and 50 are opened and closed by the axial movement of the roll pin 32. The two pairs of contacts 90 are simultaneously opened or closed by an oxygen monitor 92 which senses the partial pressure of the oxygen ($PPO_2$) in the breathing system at the inlet to the mask (not shown) and closes the contacts 90 when the $PPO_2$ is below a predetermined minimum level. An aneroid device 94 responsive to cabin pressure closes a set of contacts 96 below a pressure equivalent to an altitude of 25,000 feet. A caution light 100 gives indication of a low $PPO_2$ level. A caution light 102 gives indication that the control stem 30 has moved to the ON position. Microswitch 48 controls the OBOGS bleed flow controller 104.

MODE OF OPERATION OF THE PREFERRED EMBODIMENT

The selector valve 10 is used in an aircraft breathing system which has an on-board oxygen generating system (OBOGS) with a backup oxygen system (BOS), both used to provide oxygen enriched gas to the pilot. The selector valve employs the OBOGS and the BOS, singly or in combination, manually, as determined by the pilot, or automatically to suit the pilot, systems and/or flight conditions. The selector valve 10 has three (3) operating modes, BOS OFF, OBOGS, and BOS ON. The modes are selected by rotatively positioning the screw cam 36 by means of a selector knob 37 attached to its stem.

Referring to the Figures, in the "BOS OFF" position, the screw cam 36 drives the roll pin 32 into the valve (which motion in the exemplary illustration is to the right) displacing the stem 30 and its piston element 28, the end plate 56 and the poppet 58 seating the poppet and closing the area 62. At the same time the roll pin 32 trips the lever 40 simultaneously actuating the microswitches 48 and 50, closing the switch 48 and opening the switch 50. In this "BOS OFF" position, the selector valve 10 has restricted the BOS completely causing the OBOGS to function as though no BOS gas were available. The aneroid 94 will close the contacts 96 when the cabin pressure reaches 25,000 feet. Though the coil 69 is energized by the contacts 96 closing, and the solenoid 24 will open, there is no effect on the selector valve since the poppet 58 is held in its seat mechanically as will be more fully understood later. It should be noted that the "BOS OFF" position of the selector valve is not considered normal for flight conditions. This position provides a positive closure of the BOS to prevent inadvertent leakage when the aircraft is not in service.

In the "OBOGS" position of the selector knob 37, the microswitch 48 remains closed and the microswitch 50 remains open. The screw cam 36 allows the roll pin 32 to move to the left along with the stem 30 and its piston element 28, the end plate 56 and the poppet 58, all motivated by the compression spring 66, until the face 26 of the piston 28 contacts a land 51 of the housing 13 restricting further travel. OBOGS gas passes the restrictor 20 pressurizing the first face 26 of the piston 28 causing the piston to move, assisted by the biasing spring 47, against the bias of the compression spring 66 moving the end plate 56 and the poppet 58 seating the poppet and closing the area 62. Area 62 will be open below a preset OBOGS pressure. When the aneroid device 94 closes the contacts 96 at 25,000 feet cabin altitude and/or when the oxygen monitor 92 senses low $PPO_2$ closing the contacts 90, the coil 69 is energized, the solenoid 24 opens and the OBOGS gas pressure downstream of the restrictor 20 decays as the gas bleeds through the inlet 22 to a chamber 104 which is vented to the atmosphere. The pressure decay allows the piston 28 to be returned by the compression spring 66 to the point where it contacts the land 51, retracting the poppet 58 and opening the area 62. As the poppet 58 unseats, the pressure in the chamber 60 rises as the high pressure backup oxygen enters the inlet 16. The pressure in the chamber 60 also internally pressurizes the bellows 54 as the oxygen passes through the passage 106 in the poppet 58 expanding the bellows 54 against the spring 66 and constricting the area 62. The dynamics of the bellows operating on the area 62 are those of a conventional pressure regulator. If the pressure at the inlet 16 is high, this pressure will expand the bellows, restrict the area 62 and introduce a pressure drop at the area 62 which will reduce the pressure exiting at the port 18. If the inlet pressure at the port 16 decreases due to the depletion of the oxygen bottle or otherwise, the bellows will contract, opening the area 62, decreasing the pressure drop at the area and thereby maintaining a constant pressure at the port 18 until the inlet pressure falls below the regulated pressure level.

Summarizing the "OBOGS" position of the selector valve, the microswitch 48 is closed and the microswitch 50 remains open and under 25,000 feet altitude, the solenoid valve 24 is closed. The OBOGS gas pressure acting on the piston 28 seats the poppet 58 closing the area 62. OBOGS gas is directed to the pilot. Over 25,000 feet cabin altitude, the aneroid device 94 closes the contacts 96, energizing the coil 69 and opening the solenoid valve 24. The coil 69 will also be energized opening the valve 24, when the oxygen monitor 92 senses low $PPO_2$ and closes the contacts 90. When the valve 24 opens, OBOGS gas pressure decays as the gas bleeds off to the atmosphere and allows the piston 28 to return thereby allowing the poppet 58 to unseat and permit the bellows 54 to act on the poppet 58 and allow pressure regulated flow of backup oxygen past the exit port 18.

The third position, BOS ON, of the selector valve 10 closes the microswitch 50 and opens the microswitch 48 as the roll pin moves further to the left and disengages the trip lever 40. The screw cam 36 rotates so as to engage the dump valve 44 at its stem 42 with the crest of one of the screw cam lobes thereby opening the dump valve and venting to atmosphere the OBOGS gas downstream of the flow restrictor 20 causing the pressure acting on the face 26 of the piston 28 to decay. As the pressure decays, the piston 28 returns by the urging of the spring 66 to the position where it contacts the land 51. BOS gas is provided to the pilot. The closing of the microswitch 50 powers the lamp 102 indicating that the BOS is on.

The shuttle valve 70 is responsive to the OBOGS and BOS gas pressures. The pressure regulated BOS gas, which exits the port 18, enters the shuttle valve 70 at the port 74. Likewise, the OBOGS gas which enters the control valve 12 at the inlet 14 also enters the shuttle valve 70 at the inlet port 72. The piston 78 alternatively seats and closes and unseats and opens the inlets 80 and 82 of the chamber 84. OBOGS gas pressure acting on the piston 78 assisted by the bias of the spring 88 will seat the piston at the inlet 82 closing that inlet and directing the OBOGS gas from the inlet 72 to the chamber 84 and to the discharge port 76 which is connected to the breathing mask regulator (not shown) which breathing mask furnishes the oxygen enriched gas to the pilot. When, under the various conditions described above, the BOS gas is available at the outlet port 18, its pressure at the inlet 74 will act on the piston 86 opening the inlet 82 and seating the piston 78 at the inlet 80 blocking OBOGS gas flow and permitting BOS gas flow from the inlet 74 through the chamber 84 inlet 82 to the discharge port 76 to the pilot.

Typically, the pressure levels to which the shuttle valve 70 could be responsive are an OBOGS maximum pressure of 35 psig which will open the inlet port 80 in cooperation with the spring 88. A regulated BOS gas pressure of 45 psig will shuttle the piston 78 to close the port 80 and open the port 82 against the bias of the spring 88. Due to the area difference of the pistons 78 and 86 after initially shuttling the piston 78 at 45 psig, the valve will hold this position to BOS gas pressures as low as 20 psig. When the BOS gas pressure falls below 20 psig due to depletion or shutoff, the OBOGS product gas pressure will shuttle the valve and OBOGS gas will be furnished to the pilot.

What is claimed is:

1. A selector valve for controlling the flow of oxygen from a primary, or a secondary, backup source, singly or in combination, either selected manually or automatically to suit environmental condition, said selector valve comprising:

a three-position manual switch including a cam surface;

a slidable stem controlled by said cam surface;

a piston surface mounted on said stem and exposed on one side to a control pressure derived from the primary source;

a poppet valve for controlling the flow of oxygen from the secondary source, said poppet valve being coupled to said stem;

control pressure vent means for venting said control pressure to atmosphere, whereby, (1) in the first position of the switch the poppet valve is mechanically closed by said stem to prevent the flow of oxygen from the secondary source, (2) in the second position said control pressure maintains the poppet valve mechanically closed, and (3) in the third position said control pressure is vented to atmosphere, allowing the poppet valve to open to allow the flow of oxygen from the secondary source.

2. The selector valve of claim 1 further comprising:

a bellows coupling said poppet valve to said stem;

a passage coupling the interior of the bellows to the pressure of the secondary source, whereby pressure changes of said secondary source are reflected by said bellows causing said poppet valve to regulate the pressure of the secondary source.

3. The selector valve of claim 1 further comprising:

aneroid means for developing a signal in response to ambient pressure, whereby in the second position of the switch, said control pressure vent means may be actuated by said aneroid means to vent said control pressure to atmosphere to open the poppet valve.

4. The selector valve of claim 1 further comprising:

dump valve means for said control pressure, whereby in the third position of said switch the cam surface actuates the dump valve to vent said control pressure to atmosphere.

5. The selector valve of claim 1 further comprising:

an oxygen monitor sensing the oxygen partial pressure of the primary source, said oxygen monitor actuating the control pressure vent when the sensed oxygen partial pressure is low, allowing the secondary source to be used.

* * * * *